(12) United States Patent
Valaskovic

(10) Patent No.: US 6,190,559 B1
(45) Date of Patent: Feb. 20, 2001

(54) EVAPORATIVE PACKING A CAPILLARY COLUMNS

(76) Inventor: Gary A. Valaskovic, 694 Green St., Apt. 3, Cambridge, MA (US) 02139

( * ) Notice: Under 35 U.S.C. 154(b), the term of this patent shall be extended for 0 days.

(21) Appl. No.: 09/365,610

(22) Filed: Aug. 2, 1999

Related U.S. Application Data

(62) Division of application No. 09/087,202, filed on May 29, 1998, now Pat. No. 5,997,746.

(51) Int. Cl.⁷ .................................................. B01D 15/08
(52) U.S. Cl. .................. 210/656; 210/198.2; 210/51.01; 95/82; 95/88; 96/101
(58) Field of Search ..................................... 210/635, 656, 210/658, 198.2, 510.1; 95/82, 88; 96/101; 141/12, 80

(56) References Cited

U.S. PATENT DOCUMENTS

| | | | |
|---|---|---|---|
| H896 | 3/1991 | Szakasits et al. .................. | 210/198.2 |
| 4,483,773 | 11/1984 | Yang ..................... | 210/656 |
| 4,793,920 | 12/1988 | Cortes et al. ...................... | 210/198.2 |
| 4,966,696 | 10/1990 | Allington et al. ................ | 210/198.2 |
| 5,453,163 | 9/1995 | Yan ................................... | 204/180.1 |
| 5,679,255 | 10/1997 | Cortes et al. ......................... | 210/656 |

OTHER PUBLICATIONS

Tsuda et al., Analytical Chemistry, vol. 50, No. 2, (Feb. 1978) pp. 271–275 "Packed Microcapillary Columns in High Performance Liquid Chromatography".

Shelly et al., Analytical Chemistry, vol. 56, (1984) pp. 2990–2992 "Aids for Analytical Chemists: Dead–Volume Free Termination for Packed Columns in Microcapillary Liquid Chromatography".

Crescentini et al., Analytical Chemistry, vol. 60, (1988) pp. 1659–1662 "Preparation and Evaluation of Dry–Packed Capillary Columns for High–Performance Liquid Chromatography".

Kennedy et al., Analytical Chemistry, vol. 61, (1989) pp. 1128–1135.

Cappiello et al., Chromatographia, vol. 32, (1991) pp. 389–391 "New Materials and Packing Techniques for Micro–HPLC Packed Capillary Columns".

Fermier, et al., J. Microcolumn Separations, vol. 10, (1998) pp. 439–447 "Capillary Electrochromatography in Columns Packed by Centripetal Forces".

Li, et al., Rev. Sci. Instruments, vol. 62, (1991) pp. 2630–2633 "Polystyrene latex particles as size calibration for the atomic force microscope".

Dushkin et al., Langmuir, vol. 9, (1993) pp. 3695–3701 "Colored Multilayers from Transparent Submicrometer Spheres".

*Primary Examiner*—Ernest G. Therkorn
(74) *Attorney, Agent, or Firm*—Norris McLaughlin & Marcus P.A.

(57) ABSTRACT

Method for loading a column with a packing material by inserting one end of a column to be packed into a slurry of a packing material in a volatile solvent, allowing said slurry to be drawn into said end of said column by capillary action, withdrawing said end from said slurry, and removing said volatile solvent from the slurry that has been drawn into said end of said column, through the same end of the column at which the slurry entered, and sinteriing.

13 Claims, 5 Drawing Sheets

READY FOR SINTERING

CAPILLARY FLOW OF SLURRY

MENISCUS

EVAPORATION AT TIP

MENISCUS

EVAPORATION AT TIP

READY FOR SINTERING

Filling a tube with dense slurry by capillary action

EVAPORATIVE PACKING A CAPILLARY COLUMNS

This application is a division of Ser. No. 09/087,202, filed May 29, 1998, now U.S. Pat. No. 5,997,746.

BACKGROUND OF THE INVENTION

This invention pertains to a novel method of packing capillary columns. More particularly, the invention pertains to a method of packing capillary columns by drawing a slurry of packing material into a capillary column through capillary action, and then removing solvent from the slurry through one end of the column.

There are a variety of methods currently in use for packing capillary columns, such as those columns used in the fields of chromatography and electrospray ionization mass spectrometry (ESI-MS). The most popular methods in current use are the so-called "slurry packing" methods.

U.S. Pat. No. 5,679,255 discloses a method whereby a retaining material, such as a ceramic frit which will allow solvent, but not packing material, to pass is placed in one end of the column. A slurry of polymeric packing material in an organic solvent, such as THF, is then pumped through the column, from the end opposite that having the retaining frit. The packing material thereby accumulates in the column, while the liquid portion of the slurry passes out through the frit. This method has certain disadvantages, however. The capillary tubing used must be capable of withstanding the pressure generated by the pumping of the slurry into the tube, and necessary equipment, such as a pump and solvent recovery system must be provided.

High packing pressure may also cause deterioration of or damage to the packing material.

U.S. Pat. No. 4,483,773 discloses a method wherein an end restriction is first placed in a column, to permit the flow of solvent, but restrict the passage of particles out of the end of the column. A slurry is then caused to flow into the column, under pressure. A two-step pressure sequence is then used to first fill up the column and form a bed of particles and then to uniformly compress the bed.

This method is less than completely satisfactory, because special equipment is required to practice it.

There is therefore a need for a simple, direct method for packing capillary columns, which does not rely on special equipment for pumping or pressurizing slurries into the columns.

SUMMARY OF THE INVENTION

It has now been discovered that a slurry of packing material can be drawn up into a capillary column through capillary action and that when the solvent in the slurry is evaporated out of the slurry through the same end of the column through which the slurry entered, the packing that is originally suspended in the slurry migrates towards the end of the column to become closely packed.

In accordance with the invention, there is therefore provided a method for packing a capillary column which comprises forming a slurry of the packing material to be packed into the column, placing the slurry in a vessel, inserting one end of a capillary column into said slurry in said vessel or reservoir, drawing slurry into said column by capillary action and removing the solvent from the slurry that has been drawn into the column through the same end through which it entered the column. Preferably, the solvent is removed only from the end through which it entered the column, and it is particularly preferable that the solvent be removed through only the same end through which it entered the column, by evaporation.

Finally, after the solvent has been removed from the slurry that has been drawn into the column, leaving only the packing material that was in the slurry, a portion of the packing at the end of the column is optionally sintered.

DETAILED DESCRIPTION

Figure 1:
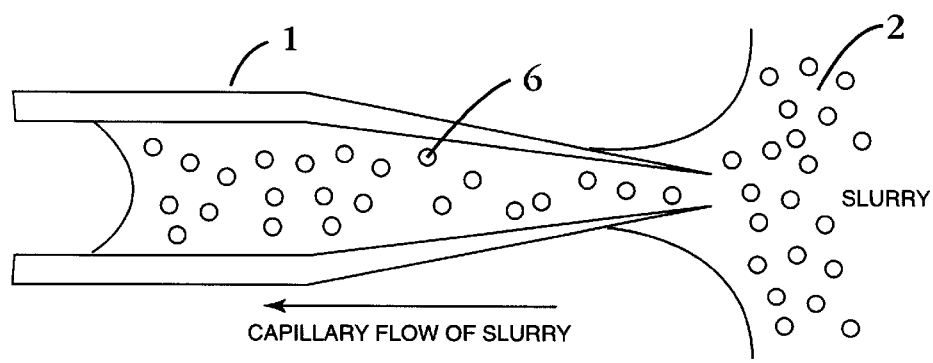
FIG. 1 is a cross sectional view of a capillary column 1 the end of which is inserted into a supply of slurry 2, which has been drawn into the capillary column.

The slurry used in accordance with the invention is a slurry of a packing material in a volatile solvent. Such slurries are prepared by mixing a packing material with a solvent.

The packing materials may be particles of a variety of shapes, such as spherical, hemi-spherical, "irregular" spheres, rods with aspect ratios of <5:1, fractured "chips" (i.e., shapes associated with finely ground materials), precipitated crystallites (tiny cubes, prisms, dodecahedral, etc.). Spherical or nearly spherical shapes are preferred, however, since such shapes allow for the most uniform and dense packing. The packing materials may be solid, hollow or porous such as, for example, solid, hollow or porous spheres.

Preferred packing materials are ceramic, metallic or polymeric. The ceramic materials which can be used include, for example, soda-lime glass, borosilicate glass, porous silica (silica gel) and non-porous silica. The metals which can be used include, for example, colloidal gold, colloidal silver, nickel and stainless steel. The polymeric materials which can be used include, for example, fluoropolymers, such as polyvinylidene fluoride (PVDF), fluorinated ethylene propylene (FEP); styrenics, such as polystyrene (PS) and polystyrene/divinylbenzene copolymer (PS/DVB); polyolefins such as high density linear polyethylene (HDPE), low-density linear polyethylene (LDPE) and polypropylene; polyketones, such as polyetheretherketone (PEEK); acrylics, such as polymethylmethacrylate (PMMA) and vinyls, such as divinylbenzene (DVB). Particularly preferred materials are borosilicate glass, silica (both porous silica and non-porous silica) and PS/DVB copolymer.

The particles which are used should have dimensions, i.e., diameters in the case of spheres, which are smaller than the smallest internal dimension of the column to be used, if the column has an internal shape other than round, or smaller than the internal diameter if the column, if the column to be used has a round internal shape, and should have maximum dimensions, or diameters if spherical, of about ½ the smallest internal dimension or diameter of the columns used. In general, the largest dimensions of non-spherical particles, or the diameters of the spherical particles used, range from about 0.1 $\mu$m to about 1 mm, although a range of 0.25 $\mu$m to about 250 $\mu$m is preferred; a range of 0.5 to 30 $\mu$m being particularly preferred, a range of 1 to 5 $\mu$m being especially preferred, and a range of 2 to 4 $\mu$m being very especially preferred.

There are many solvents known to the art which can be used to form the slurry. Preferred solvents are methanol, acetone and tetrahydrdrofuran (THF), although almost any volatile solvent can be used. The solvent selected should, of course, be one that will not dissolve, swell or otherwise harm the packing material selected, although it should "wet" the surface of the packing material.

The capillary tubes which are used for the columns are those known to the art, and can, for example, be those which are generally classified as ceramics, such as borosilicate glass, fused-silica, polyimide coated fused-silica and aluminum coated fused-silica; metallic, such as stainless steel, glass lined stainless steel or silica lined stainless steel; or they can be of polymeric materials. The polymeric material which can be used include fluoropolymers, such as ethylene tetrafluoroethylene (ETFE), fluorinated ethylene propylene (FEP) and polytetrafluoroethylene(PTFE); polyolefins, such as high density linear polyethylene (HDPE), low-density linear polyethylene (LDPE) and polypropylene; polyketones, such as polyetheretherketone (PEEK) and silica-lined PEEK; acrylics, such as polymethylmethacrylate (PMMA), polyamides, such as nylon 6, nylon 11 and nylon 12; and polyimide., Preferred capillary tubing for use as capillary columns in accordance with the invention are those of polyamide-coated fused silica, stainless steel, PEEK and HDPE, although polyimide-coated fused silica is especially preferred.

The internal or external shapes of capillary columns used in the practice of this invention can take on a variety of regular geometric shapes, such as round, oval, square, rectangular, polygonal, such as pentagonal, hexagonal, and the like; or can take on irregular shapes. The term "internal shape" of the capillary columns, as used herein, has the same meaning as the "bore" of a capillary column. Particularly preferred are those columns having a round internal shape or bore.

The columns used in the practice of the invention, having round internal shapes or bores, have inside diameters in the range of from about 1 $\mu$m to about 2 mm, preferably 5 to 250 $\mu$m and particularly preferably 20 to 100 $\mu$m. Where columns having internal shapes other than round are used, their internal cross-sectional areas should be in the same range as that of a column having a round internal shape with a diameter in the range of from about 1 $\mu$m to about 2 mm, preferably that of a column having a round internal shape with a diameter 5 to 250 $\mu$m and particularly preferably that of a column having a round internal shape with a diameter 20 to 100 $\mu$m The columns can be of uniform internal dimensions or diameter over their entire length, such as those typically used as chromatography columns, or they can be tapered at one end, so that the internal diameter tapers to a narrow tip or needle, such as those columns used for electrospray ionization mass spectrometry (ESI-MS). The columns having tapered ends are also referred to in the art as needles. FIGS. 1–7 illustrate the ends, or tips, of the tapered-end columns, also referred to as needles. Where such tapered-end columns are used, the end or tip of the column, also referred to as the end of the needle, which is the end of the column where the packing is to be loaded, has an internal diameter ranging from about 1 $\mu$m to about 100 $\mu$m, preferably from 5 to 30 $\mu$m, particularly preferably 10 to 20 $\mu$m, especially preferred is a diameter of 15 $\mu$m. The length of the tapered portion, meaning the length of column over which the diameter tapers from the internal diameter of the untapered portion of the column to the internal diameter of the tip ranges from about 0.1 to 10 mm, preferably from 0.25 to 3 mm, especially preferably from 0.5 to 1.5 mm.

The length of the columns to be used will vary with the contemplated application, as well as the amount of additional packing, if any, which is to be used in combination with the packing of the present invention. That is to say, the packing of the present invention can be used alone, or in combination with other packings which can be added to the column before or after the present packing. Packed columns with lengths of 19 meters or more are known (U.S. Pat. No. 4,793,920), and such columns can be used in the practice of this invention, for which the length of the column used is not limited. As will be understood by those skilled in the art, however, the amount of packing that can be packed into a column using the method of this invention is limited by the capillarity between the slurry of packing material and the capillary column, which results in a specific theoretical maximum capillary height for each combination of slurry composition and capillary column composition, at given ambient conditions. The maximum capillary height for any particular application can easily be determined by simply inserting one end of the capillary column into the slurry, and observing how high into the column the slurry is drawn.

The slurry can be prepared by conventional methods, known to those skilled in the art. One such method is simple mixing, wherein a solvent is introduced into a vessel, such as a vial, beaker or a flask, together with the packing material, and the contents are then stirred. The capillary tube can then be inserted into the thus prepared slurry in the vial, beaker or flask, whereupon the slurry is drawn into the capillary tube by capillary action. The slurries according to the invention are formed with about 0.002 to 8 grams of packing per ml of solvent, preferably 0.03 to 5 grams of packing per ml of solvent, particularly preferably 0.2 to 1 gram packing per ml of solvent.

Figure 8:
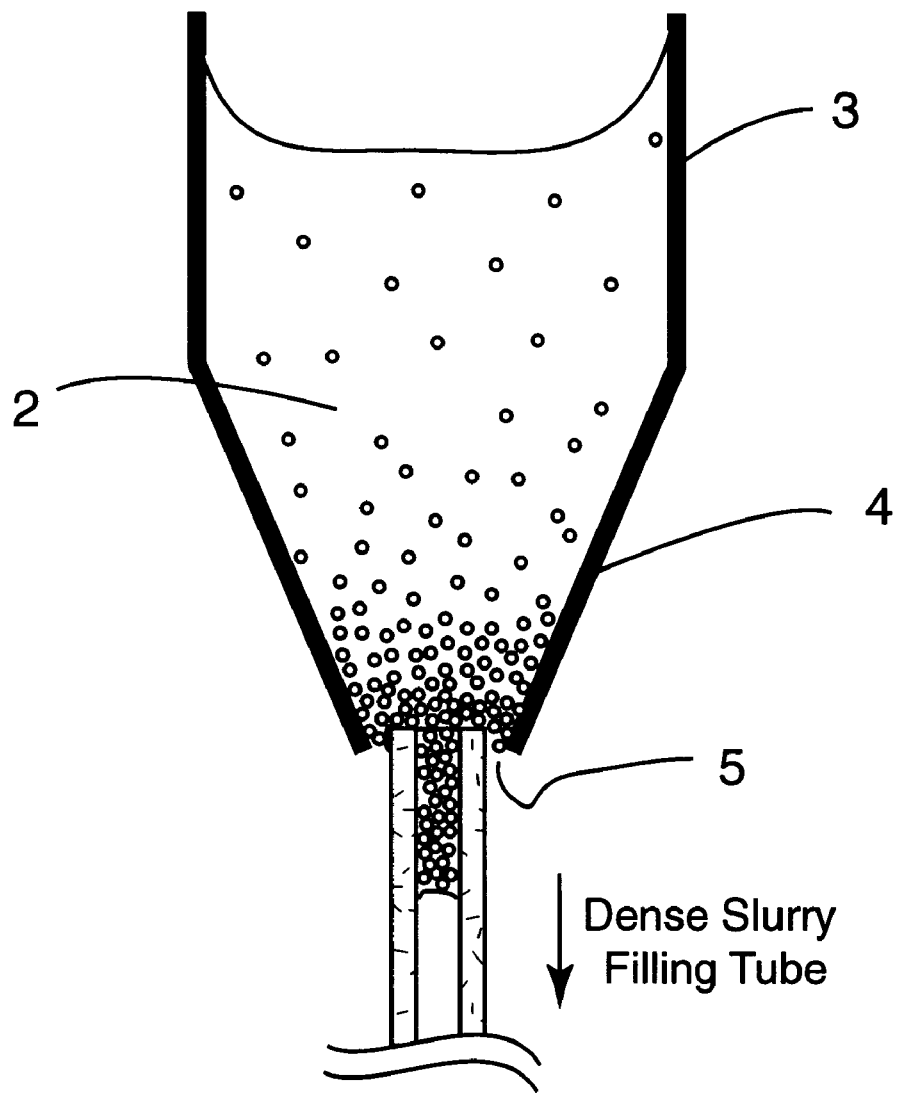
FIG. 8 is a cross sectional view of a vessel 3 having a conical bottom 4 with a hole 5 into which capillary 1 has been inserted whereby slurry 2 is drawn into column 1 by capillary action.

Alternatively, the slurry can be transferred from the vessel in which it was prepared into another vessel, such as a vessel having a conical bottom with a hole at the apex of the conical bottom, such as is shown in FIG. 8. One such vessel which can be used in accordance with the invention, is a common polyethylene pipette tip. In yet another embodiment of the invention, a vessel having a conical tip with a hole in the apex of the cone and a septum in the hole can be used. When using such vessels, the capillary tube is inserted into the slurry through the hole or, if the hole in the vessel is equipped with a septum, through the septum.

The time required to draw the slurry into the capillary tube by capillary action varies, depending upon a variety of factors, such as the dimensions of the packing material, i.e., the diameter of the spherical packing material, as well as the density of the slurry and the inside diameter of the capillary tube. In general, however, the slurry will be drawn into the capillary virtually instantly upon insertion of the tube into the slurry. Depending upon the extent to which it is desired to fill the capillary tube with packing, more or less time will be required. If it is desired to pack only the tip of the capillary tube, to form a frit, for example, the desired amount of packing can be drawn in less than one second. If, on the other hand, it is desired to fill the column to the maximum achievable extent, known as the "full capillary height", several hours may be required. In general, however, the desired amount of slurry can be drawn into the capillary tube in from about 0.1 second to about 2 hours, although in most cases it will require only from about 0.1 second to about 30 minutes. The time required will, of course, vary depending upon the particular nature of the slurry and that of the capillary tube, as well as the conditions at which the filling is being conducted, such as temperature and pressure. Although it is possible to conduct the filling operation at elevated temperature and either elevated or reduced pressure, satisfactory results are generally obtained at ambient temperature and pressure.

Where no septum is used, the hole in the conical bottom of the aforedescribed vessel should be of such a size that the surface tension of the solvent in the slurry will prevent passage of slurry through the hole. Such holes will range in size from a diameter of about 0.1 mm to about 3 mm, preferably about 0.3 mm to about 1 mm.

A particular advantage of using such conical bottomed vessels is that the slurry, once placed in said vessel, can be allowed to settle, thereby forming a higher concentration of packing per ml of solvent in the bottom of the vessel, and the slurry that is drawn into the capillary tube from the vessel will thus have a higher concentration of packing than the original slurry.

A further advantage of using a conical bottomed vessel is that, as the slurry settles out in the conical bottom, a concentration gradient is formed, whereby the concentration of particles in the solvent gradually increases from the top of the vessel to the bottom. The density of the slurry that is drawn into a capillary tube inserted into the hole at the apex of the cone in the conical bottom of the vessel can then be controlled by varying how far the tube sticks up into the vessel. The closer the end of the capillary tube is to the bottom of the cone, the higher the density of the slurry drawn into the capillary tube will be.

In a particularly preferred embodiment, the slurry comprises glass microspheres as packing material in methanol as solvent, at concentration of about 0.2 grams of microspheres per ml of methanol.

In a particularly preferred embodiment of the invention, the packing material in the column is sintered, after the solvent has been removed. The packing is sintered by applying energy to it. This is done by heating the packing material with a heat source, such as hot air, by laser radiation, microwave heating or a combination of such heating means. The amount of heat applied is controlled to be sufficient to sinter the packing material, while avoiding melting it. A sufficient amount of heat must be applied so as to cause the packing material to soften. (For glass, silica or polymeric materials, the glass transition temperature must be reached.) Heating time and temperature must be sufficient to cause the particles to fuse together, but not so long or so hot as to eliminate all of the inter-particle spacing and voids. Complete melting of the packing material is, of course, to be avoided.

In the practice of this invention, the slurry is drawn into the capillary column, as described above, through capillary action. Then, the solvent that is in the slurry that has been drawn into the column is removed from the slurry through the same end of the column through which the slurry entered the column. Preferably, the solvent is removed from the slurry by evaporation. In conducting the evaporation of the solvent, the column can be allowed to stand in ambient air, as, for example may exist in a fume hood, or by passing a stream of a gas, such as air or nitrogen, over the tip of the end, to accelerate evaporation. The rate of evaporation can be controlled by such factors as the rate of gas which is passed over the tip of the end of the column, as well as the ambient temperature and the temperature of the gas that is passed over the tip of the end of the column.

Alternatively, the solvent can be removed through the end of the column by other means, such as "blotting", by holding an absorbent material, such as a filter paper or membrane, over the end of he column to contact and draw solvent out of the column.

In one embodiment of the method of the invention, a slurry that is close to the theoretical maximum density of particles suspended in a unit volume of solvent is used. In such a case, the dense slurry, when drawn into the end of the capillary tube, will remain tightly localized near the end of the capillary tube and, when the solvent is evaporated, the meniscus packs the slurry into a tight slug of material.

In yet another embodiment, the capillary tube is pre-filled with solvent, and then a portion of the solvent is permitted to evaporate, leaving an air gap at the end of the column. The end with the air gap is then inserted into the slurry, whereby the amount of slurry that is drawn into the column is limited by the air gap between the entering slurry and the pre-filled solvent. Then, the solvent, including both the pre-filled solvent and the solvent of the slurry is evaporated. As the solvent evaporates, the meniscus movement packs the packing material into a tight porous plug at the end of the tube.

Referring now to the drawings, FIG. 1 shows the end tip of a tapered-end capillary column 1, also referred to as a needle, of the present invention. As shown, the capillary tube is inserted into a reservoir of slurry 2, comprising packing spheres 6 dispersed in a solvent, and the slurry has been drawn into the tube by capillary action.

Figure 2:
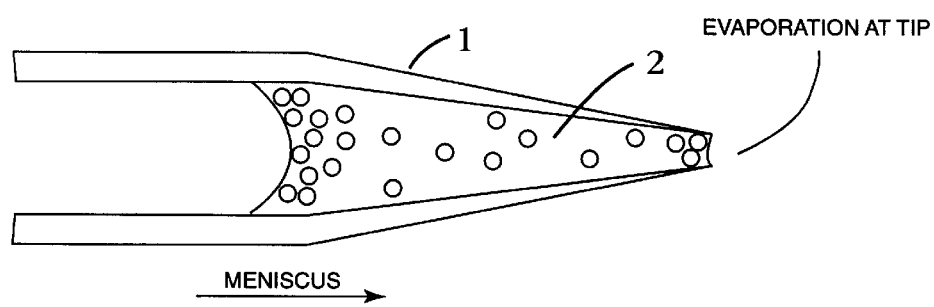
FIG. 2 is a cross sectional view of the capillary column of FIG. 1 after evaporation of a part of the solvent from slurry 2 through the same end of the column through which the slurry originally entered the column.

FIG. 2 shows the capillary tube end-tip of FIG. 1, after partial evaporation of the solvent out of the end-tip. As is illustrated, the meniscus of the surface of the slurry inside the column and furthest removed from the end tip of the column has moved towards the end tip, as solvent is evaporated from the end tip. As also illustrated, and this is an important feature of the present invention, the meniscus, as it moves towards the end-tip, brings with it a concentration of the packing material, so that as the solvent is evaporated from the end-tip, the slurry concentrates itself towards the end-tip. This is entirely surprising, as the packing material would have been expected to "precipitate out" of the solvent, and be left behind in a dry state, as the volume of solvent shrinks towards the end tip. It was not to be expected that the moving meniscus would actually carry the packing material towards the end-tip, thereby concentrating the packing material in the direction of the end tip. It has now been discovered that as the liquid solvent evaporates, the meniscus traveling towards the end of the tube collects and gently forces the packing material towards the end of the tube. The surface tension of the liquid/air (or liquid/nitrogen) interface at the end of the tube is sufficient to hold the packing material in place in the slurry against this gentle moving force. The tube may optionally be vibrated and/or slowly rotated on its axis during the evaporation process to promote dense packing of the packing material.

Figure 5:
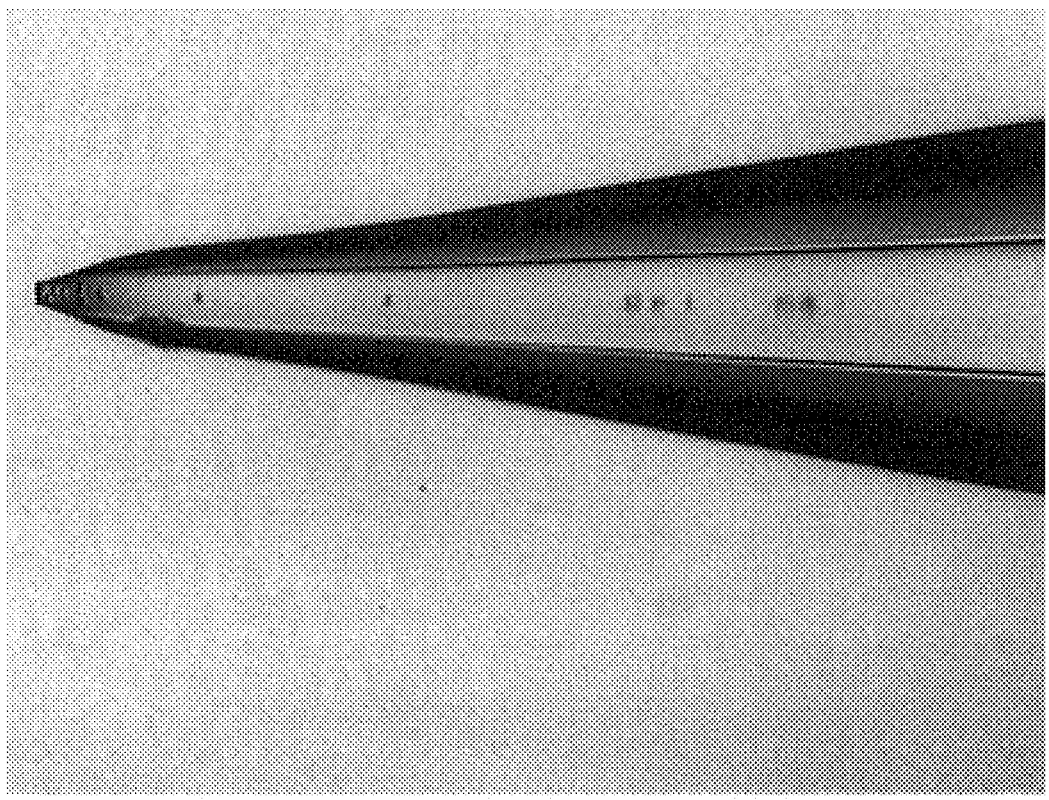
FIG. 5 is a photograph of the end of a capillary column into which a slurry of packing material has been drawn by capillary action.

FIG. 5 is an actual photograph of a capillary tube such as that illustrated in FIG. 2.

Figure 3:
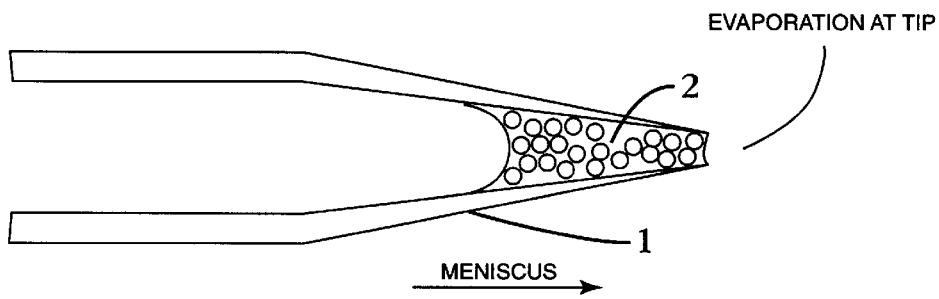
FIG. 3 is a cross sectional view of the capillary column of FIG. 2 after further evaporation has taken place.

FIG. 3 illustrates the column of FIG. 2 after further evaporation has taken place, whereby the concentration of the packing material has been further increased and moved closer to the end-tip.

Figure 6:
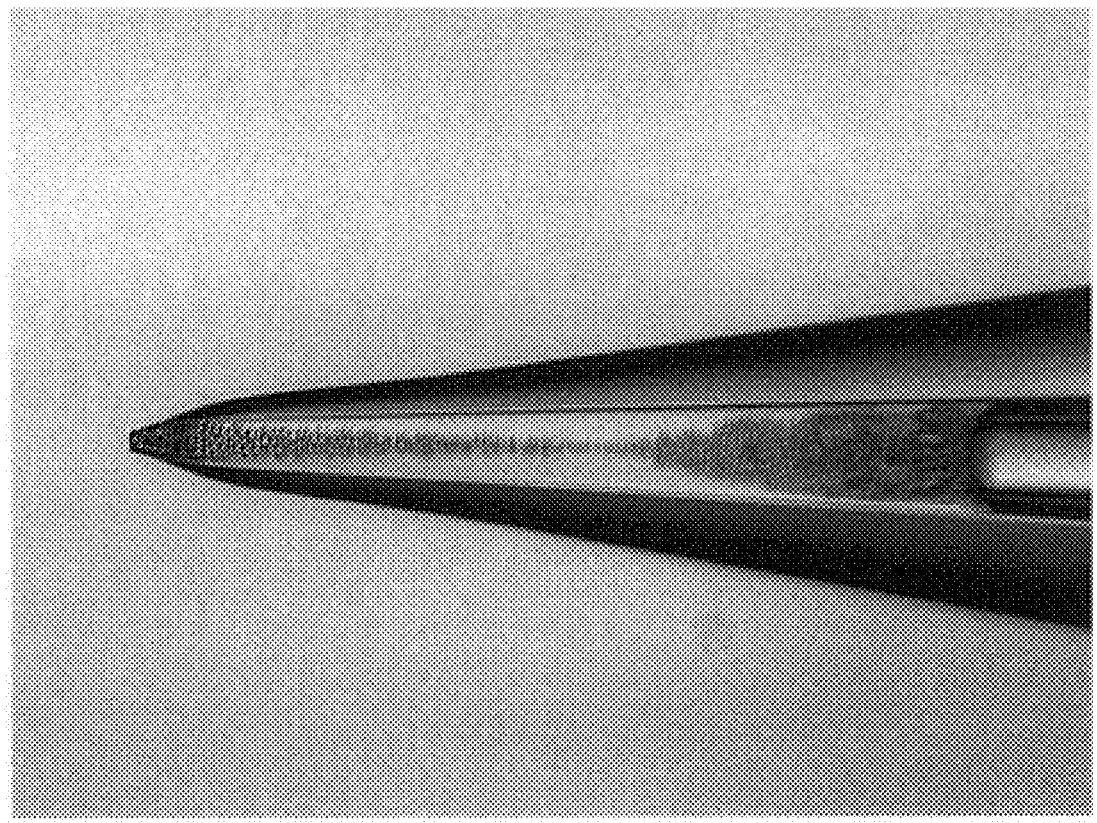
FIG. 6. is a photograph of the capillary column of FIG. 5, after partial evaporation of the solvent in the slurry has taken place, out of the end of the column.

FIG. 6 is an actual photograph of a capillary tube such as that illustrated in FIG. 3.

Figure 4:
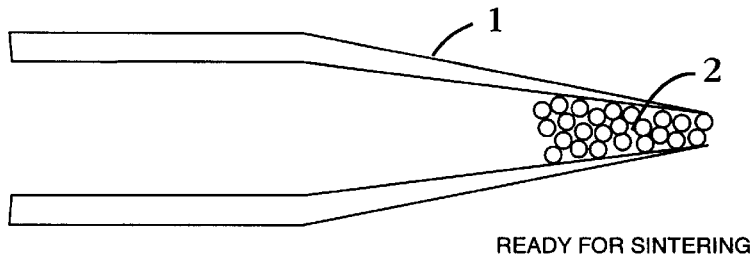
FIG. 4 is a cross sectional view of the capillary column of FIG. 3, after complete evaporation of the solvent has taken place.

FIG. 4 illustrates the column of FIG. 3 after all of the solvent has been evaporated. The packing material illustrated in FIG. 4, with the solvent removed, is ready for sintering.

Figure 7:
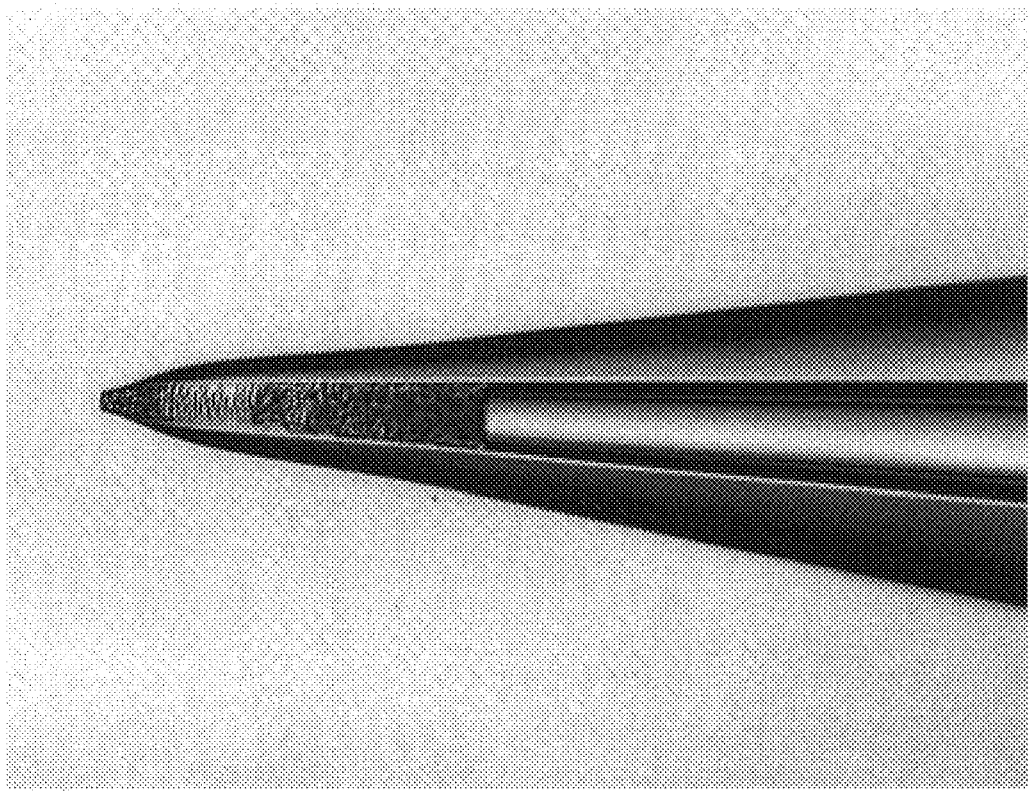
FIG. 7 is a photograph of the capillary column of FIG. 6, after further evaporation has taken place.

FIG. 7 is an actual photograph of a capillary tube such as that illustrated in FIG. 4.

The method of the present invention can be better understood by reference to the following example, but is not limited thereby.

EXAMPLE 1

A 10 cm long piece of 360 $\mu$m outside diameter (OD), 75 $\mu$m inside diameter (ID) polyimide coated fused silica tubing (Polymicro Technologies, Phoenix, Ariz.) was mounted in a commercial laser-heated micropipette puller (Sutter Instruments, Novato, Calif.) and drawn down into two sharp needles so that the internal diameter at the needle end was reduced to 15 $\mu$m.

A slurry of 5 $\mu$m diameter solid glass microspheres was prepared by mixing 0.1 gram of the spheres with 0.5 milliliters of 100% methanol in a small (1 ml) glass vial. The mixture was stirred thoroughly for 5 minutes, ultrasonicated for 5 minutes, and then allowed to settle for 2 hours. After removing the excess solvent above the slurry, which had settled to the bottom of the vial, approximately 10 $\mu$l of slurry was transferred to a polyethylene vessel (a commercial polyethylene pipette tip) possessing a conical bottom having a 0.5 mm hole at it's apex. The slurry was again allowed to settle for approximately 5 minutes, while holding the pipette tip in the vertical position.

Both the slurry-containing vessel and the silica needle were mounted horizontally on the stage of a standard light microscope and viewed at 100-× magnification. The microscope stage had an additional translation stage that allowed the silica needle to be moved into the hole of the pipette tip. By moving the tip into brief contact ($\approx$0.5 seconds), with the slurry through the hole, approximately 75–100 microspheres were transferred into the silica needle.

The needle was allowed to rest on the stage of the microscope for 5 minutes while the methanol completely evaporated from the tip of the needle. During this time, the silica was packed into place by the movement of the meniscus.

The needle was transferred to a device holding a platinum foil heating element with a 3 mm "trough" filament, 3 mm wide (Sutter Instruments filament number FT330B). The end of the needle containing the packed spheres was centered in the filament. The filament was energized for 12 seconds with a heat output of 20.1 watts, to sinter the microspheres.

EXAMPLE 2

The procedure of Example 1 was repeated, except that a needle fabricated from 50 $\mu$m ID fused silica tubing pulled down to an 8 $\mu$m ID tip was used. Approximately 25–50 spheres were transferred into the end of the silica needle. For sintering, the heat output of the filament device was reduced to 19.4 watts.

EXAMPLE 3

The procedure of Example 1 was repeated, but a 10 cm piece of 50 $\mu$m ID, 360 $\mu$m OD polyimide coated, fused silica tubing was cut with a clean square end-face. The slurry was prepared as in Example 1, but 10 $\mu$m highly porous spheres of poly(styrene-divinylbenzene(Poros®, Perspective Biosystems 10-R2) were substituted for the glass microspheres. The column was loaded as described in Example 1. The packing was sintered in the same apparatus to form a frit, but the heating conditions were 3 seconds at 6.3 watts

EXAMPLE 4

A 25-cm length of 75 $\mu$m ID tubing was cleaved to have a flat end-face.

A slurry was prepared as in Example 1. After settling, 100 $\mu$l of slurry was transferred to a polyethylene pipette tip. The tip was held in the vertical position and the slurry allowed to settle for 15 minutes. Settling time was monitored with a light microscope to ensure that >95% of the material had settled out to the bottom of the tip.

While left in the vertical position, the silica capillary tube was inserted approximately 50 $\mu$m into the hole at the bottom of the pipette tip. The dense (nearly opaque) slurry filled the silica tube by capillary action. The tube was left in contact with the slurry until 15 cm of the tube was filled.

Upon removal, the end of the silica tube was brought into contact with a Nylon filter pad (Milipore Corp.), and mounted horizontally on the stage of a light microscope. The movement of the meniscus and packing of the column was monitored for approximately 45 minutes. When evaporation appeared to be complete, the Nylon filter paper was removed and packing material at the end of the tube was sintered into a frit by heating in the heating device described in Example 1, with a filament output of 25 watts for 12 seconds.

EXAMPLE 5

The procedure of Example 4 was repeated, except that the filling was accomplished with the tube in the horizontal position. A column with 10 cm of packed material was thereby fabricated.

The invention and its advantages are readily understood from the foregoing description. It is apparent that various changes can be made in the process without departing from the spirit and scope of the invention. The process as herein presented, is merely illustrative of preferred embodiments of the invention, and not a limitation thereof.

I claim:

1. A method for loading a column with a packing material which comprises forming a slurry of a packing material in a volatile solvent, inserting one end of a column to be packed into said slurry, allowing said slurry to be drawn into said end of said column by capillary action, withdrawing said end from said slurry, and removing said volatile solvent from the slurry that has been drawn into said end of said column, through the same end of the column at which the slurry entered.

2. The method of claim 1, wherein said solvent is removed from said slurry that has been drawn into said end of said column, by evaporation.

3. The method of claim 1, wherein said solvent is removed from said slurry that has been drawn into said end of said column, by absorption onto an absorbent.

4. The method of claim 1, wherein said absorbent is filter paper or membrane.

5. The method of claim 1, wherein said packing material is a sinterable packing material and wherein, after said solvent has been removed, energy is applied to said sinterable packing to sinter it.

6. The method of claim 5, wherein said energy is in the form of heat, a laser beam or microwave radiation.

7. The method of claim 5, wherein said sinterable material is glass, silica, metal or polymer.

8. The method of claim 7, wherein said sinterable material is glass, in the form of spheres having a diameter of from about 0.25 $\mu$m to about 250 $\mu$m.

9. The method of claim 7, wherein said sinterable material is silica, in the form of spheres having a diameter of from about 0.25 $\mu$m to about 250 $\mu$m.

10. The method of claim 1, wherein said column is a hollow capillary tube of fused silica, having an inside diameter of from about 1 $\mu$m to about 2 mm.

11. The method of claim 10, wherein said inside diameter is from about 5 $\mu$m to about 250 $\mu$m.

12. The method of claim 1, wherein said end of said capillary tube is tapered.

13. The method of claim 12, wherein said capillary tube has an internal diameter of from about 20 $\mu$m to about 100 $\mu$m, and said tapered end is tapered to a tip having an internal diameter of from about 2 $\mu$m to about 30 $\mu$m.

\* \* \* \* \*